US011083492B2

United States Patent
Lin et al.

(10) Patent No.: US 11,083,492 B2
(45) Date of Patent: Aug. 10, 2021

(54) METHOD FOR IMPLANTING AN INTERVENTIONAL MEDICAL DEVICE

(71) Applicant: LIFETECH SCIENTIFIC (SHENZHEN) CO., LTD, Shenzhen (CN)

(72) Inventors: Yixian Lin, Shenzhen (CN); Anning Li, Shenzhen (CN); Shuo Shan, Shenzhen (CN)

(73) Assignee: LIFETECH SCIENTIFIC (SHENZHEN) CO., LTD, Shenzhen (CN)

( * ) Notice: Subject to any disclaimer, the term of this patent is extended or adjusted under 35 U.S.C. 154(b) by 492 days.

(21) Appl. No.: 16/001,533

(22) Filed: Jun. 6, 2018

(65) Prior Publication Data
US 2019/0374251 A1  Dec. 12, 2019

(51) Int. Cl.
*A61B 17/34* (2006.01)
*A61B 5/107* (2006.01)
(Continued)

(52) U.S. Cl.
CPC ........ *A61B 17/3468* (2013.01); *A61B 5/1076* (2013.01); *A61B 6/481* (2013.01); *A61B 6/487* (2013.01); *A61B 8/0883* (2013.01); *A61B 8/12* (2013.01); *A61B 17/3403* (2013.01); *A61B 34/20* (2016.02); *A61B 8/14* (2013.01);
(Continued)

(58) Field of Classification Search
CPC ... A61B 17/3468; A61B 6/487; A61B 5/1076; A61B 6/481; A61B 8/12; A61B 17/3403; A61B 34/20; A61B 8/0883; A61B 2017/00632; A61B 8/14; A61B 2017/3413; A61B 5/0036; A61B 5/0035; A61B 5/0044; A61B 6/12; A61B 2090/376; A61B 5/055; A61B 6/503; A61B 6/032; A61B 2017/1205; A61B 17/12172; A61B 17/12122; A61B 17/3478; A61B 2017/00247; A61B 17/12099; A61B 17/0482; A61B 90/37; A61B 2034/2046;
(Continued)

(56) References Cited

U.S. PATENT DOCUMENTS

2005/0038470 A1* 2/2005 van der Burg ... A61B 17/12172
606/213
2006/0135962 A1* 6/2006 Kick ..................... A61M 25/09
606/108

(Continued)

*Primary Examiner* — Joanne M Hoffman
*Assistant Examiner* — Nicholas A Robinson
(74) *Attorney, Agent, or Firm* — Maier & Maier, PLLC (57) ABSTRACT

A method for implanting an interventional medical device, including the following steps: delivering the distal end of the puncture needle into the right atrium via the inferior vena cava; locating the puncture site on atrial septum under X-ray fluoroscopy in a first perspective angle and a second perspective angle, and puncturing the atrial septum by the puncture needle through the puncture site; delivering the medical device to the left atrial appendage or left atrium for release under X-ray fluoroscopy in a first perspective angle. The implanting method of the disclosure does not require the use of a TEE device during implementation and provides benefits of a simple operation, short operation time, and easy implementation conditions, while also be easy to promote and popularize.

13 Claims, 4 Drawing Sheets

(51) Int. Cl.
*A61B 8/12* (2006.01)
*A61B 6/00* (2006.01)
*A61B 34/20* (2016.01)
*A61B 8/08* (2006.01)
*A61B 17/00* (2006.01)
*A61B 8/14* (2006.01)

(52) U.S. Cl.
CPC ........... *A61B 2017/00632* (2013.01); *A61B 2017/3413* (2013.01)

(58) Field of Classification Search
CPC ........... A61B 6/48; A61B 6/485; A61B 17/00; A61M 25/065
See application file for complete search history.

(56) References Cited

U.S. PATENT DOCUMENTS

| | | | | |
|---|---|---|---|---|
| 2011/0007071 | A1* | 1/2011 | Pfister | A61B 34/10 345/419 |
| 2013/0321262 | A1* | 12/2013 | Schecter | G06F 19/00 345/156 |
| 2014/0039303 | A1* | 2/2014 | Kanzaki | A61B 6/504 600/424 |
| 2014/0128417 | A1* | 5/2014 | Shen | A61P 43/00 514/266.24 |
| 2019/0000551 | A1* | 1/2019 | Sone | A61B 6/5235 |

\* cited by examiner

METHOD FOR IMPLANTING AN INTERVENTIONAL MEDICAL DEVICE

FIELD

The disclosure relates to the technical field of interventional medical device, and in particular to a method for implanting an interventional medical device.

BACKGROUND

Thromboembolism is a serious complication of atrial fibrillation (AF). The left atrial appendage is the main site of thrombosis in patients with atrial fibrillation. Left atrial appendage thrombus falling off will cause thromboembolism in the body. In cerebral apoplexy of patients with non-valvular disease caused by AF, 90% of emboli originate from the left atrial appendage. Strategies for prevention of thromboembolism include the restoration and maintenance of sinus rhythm, oral anticoagulation, and left atrial appendage occlusion. Methods for restoring and maintaining sinus rhythm include drug therapy and catheter ablation therapy. Catheter ablation can theoretically cure AF. Oral anticoagulants have also been the main method for prevention of thromboembolism in patients with AF, but in clinical practice, oral anticoagulants have disadvantages such as poor compliance, increased risk of bleeding, and need for long-term use. For AF with no response to drug therapy or that is unable to be cured by catheter ablation, the traditional method for preventing thrombosis is oral Warfarin anticoagulation. However, long-term oral Warfarin has many problems: narrow therapeutic window, regular monitoring of coagulation function, frequent dose adjustment, easy interaction with food or other drugs, and easy bleeding. Percutaneous left atrial appendage occlusion has the advantages of less trauma, safety and reliability, and does not require long-term anticoagulation after surgery, and is another option for preventing thromboembolism in patients with AF.

However, the existing left atrial appendage occlusion is difficult and complicated to perform surgery. It is necessary to use TEE (Transesophageal Echocardiography) equipment during surgery to perform left atrial appendage occlusion, which imposes strict requirements in physicians and the entire surgical team conducting left atrial appendage occlusion, and the surgery can only be performed in hospitals that have the conditions of the equipment, resulting in higher surgical conditions, difficulty in surgery, and difficulty in popularization.

In addition, general anesthesia is required for patients undergoing surgery using TEE equipment, which will also lead to many problems: the surgery cannot be performed smoothly when patients have TEE contraindications, surgical conditions are not ready for general anesthesia, and patients need to avoid general anesthesia; after the general anesthesia is performed, the patient is in a state of unconsciousness, and physicians cannot understand the patient's condition in the surgery (for example, physicians cannot find sudden embolism (if any) in the surgery in time); patients awakening after surgery and postoperative management are more complicated and difficult; the implementation of general anesthesia requires the cooperation of anesthesiologists, but, in many hospital systems, cross-divisional coordination will be inconvenient to reach.

SUMMARY

Based on this, it is desired to provide a new method for implanting an interventional medical device in view of the technical problems the existing left atrial appendage occlusion brought about by the reliance on use of the TEE equipment.

A method for implanting an interventional medical device, including the following steps:

delivering a distal end of a puncture needle into a right atrium via an inferior vena cava; locating a puncture site on an atrial septum under X-ray fluoroscopy in a first perspective angle and a second perspective angle, and puncturing the atrial septum by the puncture needle through the puncture site;

delivering the medical device to a left atrial appendage or a left atrium for release under X-ray fluoroscopy in the first perspective angle.

In one of the embodiments, further comprising, before the step of delivering the distal end of the puncture needle into the right atrium via the inferior vena cava, puncturing a femoral vein after local anaesthesia is administered to a recipient.

In one of the embodiments, before the step of puncturing the femoral vein after local anaesthesia is administered to the recipient, performing preoperative examinations on the recipient to obtain required measurement data.

In one of the embodiments, the required measurement data comprises at least the size of the left atrial appendage's opening and the depth of the left atrial appendage's cavity.

In one of the embodiments, the preoperative examination comprises one of the followings: a TEE examination, a TTE examination, and an examination using bolus injection contrast medium.

In one of the embodiments, the first perspective angle is 30±5° to a right anterior oblique, and the second perspective angle is 45±5° to a left anterior oblique.

In one of the embodiments, the step of locating the puncture site on atrial septum under X-ray fluoroscopy in a first perspective angle and a second perspective angle, and puncturing the atrial septum by the puncture needle through the puncture site comprises: performing X-ray fluoroscopy in the second perspective angle, and initially positioning the distal end of the puncture needle to a position of a fossa ovalis;

performing X-ray fluoroscopy in the first perspective angle, determining suitable reference object within a visually-viewing heart part under X-rays, and determining a puncture site in combination with an anatomical structure of the heart; moving the distal end of the puncture needle from the fossa ovalis to the puncture site, adjusting it to be perpendicular to the atrial septum, and puncturing the atrial septum.

In one of the embodiments, the position of the puncture site is determined by a first cross point formed by a first segment and a third segment that is parallel with a second segment, and wherein the second segment is determined by two endpoints formed by a cross of a straight line atrioventricular sulcus is on with a heart boundary; the first segment is perpendicular to the second segment and their second cross point is at ⅓ of a length of the second segment and proximate to a rear of the heart, and the second cross point is one of the endpoint of the first segment, the other endpoint of which is on an upper boundary of the atrium; and a distance from the first cross point to the second cross point is ⅓ of the length of the first segment.

In one of the embodiments, the reference object is atrioventricular sulcus.

In one of the embodiments, the puncture needle is contained in a sheath, and the step of delivering the medical device to the left atrial appendage or the left atrium for release under X-ray fluoroscopy in the first perspective angle comprises:

moving a sheath to a left upper pulmonary vein; withdrawing the puncture needle from the sheath in the left upper pulmonary vein; after performing the radiography in the left atrial appendage or the left atrium, delivering the distal end of the sheath into the left atrial appendage or the left atrium; delivering the medical device via the sheath and releasing the medical device near the left atrial appendage or the left atrium.

In one of the embodiments, the interventional medical device is a left atrial appendage occluder.

In one of the embodiments, the medical device is connected with a transport rod during an implantation process, and the implanting method further comprises:

after releasing the medical device and before disconnecting it with the transport rod, injecting a contrast medium from at least two different viewing angles to assess the hermeticity of the medical device.

In one of the embodiments, a positive side position of the proximal end of the medical device is selected for observation, and the contrast medium is injected with two observation angles in 90 degrees difference to assess the hermeticity of the medical device.

In one of the embodiments, the medical device is connected with a transport rod during an implantation process, and the implanting method further comprises:

after releasing the medical device and before disconnecting it with the transport rod, injecting a contrast medium and at the same time observing a positional relationship between an edge of the medical device and a left upper pulmonary vein ostium and a bicuspid valve to determine whether interference by the device occurs.

In one of the embodiments, further comprising, before the step of locating the puncture site on atrial septum under X-ray fluoroscopy in a first perspective angle and a second perspective angle, and puncturing the atrial septum by the puncture needle through the puncture site, performing a bolus injection of contrast medium into the right atrium or pulmonary artery, and observing structure of the left atrium for 5-10 seconds after the bolus injection to obtain desired measurement data.

The method for implanting an interventional medical device can accurately locate the puncture site only through X-ray fluoroscopy under two different perspective angles, completely replacing the conventional left atrial appendage occlusion surgery that is required to use TEE to locate the atrial septum puncture site.

On the other hand, compared with the conventional surgical method, the above-mentioned implantation method does not require the use of TEE during the surgery, thereby reducing unnecessary operations and the difficulty of the surgery. Simpler operations, shorter surgery time coupled with lower requirements for operating room equipments make its popularization available.

BRIEF DESCRIPTION OF THE DRAWINGS

Further descriptions are made to the present disclosure in combination with accompanying drawings and embodiments as follows. In the drawings.

DETAILED DESCRIPTION

The present disclosure will now be described in detail with reference to the drawings representing preferred embodiments to more clearly clarify the purpose, technical solution and advantages of the disclosure. It should be understood that the preferred embodiments described herein are only to explain the disclosure and are not intended to limit the disclosure.

It should be noted that, in the field of interventional medical devices, generally the end of the medical device implanted in the human or animal body that is closer to the operator is called the proximal end, whereas the end that is farther from the operator is called the distal end. Therewith the proximal and distal ends of any component of a medical device are defined based on such principle.

The technical scheme of the present disclosure will now be further described in detail with reference to specific embodiments thereof.

Embodiment

This embodiment proposes a method for implanting an interventional medical device, which applies to implanting an interventional medical device in the vicinity of the left atrial appendage or the left atrium, particularly to implanting a left atrial appendage occluder in the vicinity of the opening of the left atrial appendage. It should be noted that the interventional medical device may be, but is not limited to, a left atrial appendage occluder. Any interventional medical device that can be implanted by the implantation method in the present embodiment is applicable, and the interventional medical device has both the compressed state contained in the outer sheath and the expanded state placed outside the outer sheath after releasing. In this embodiment, the implanting of a left atrial appendage occluder is taken as an example in detailed description. The structure of the left atrial appendage occluder may be, but is not limited to, the structure shown in FIG. 1. The left atrial appendage occluder 100 in FIG. 1 includes a flat sealing disk 110 and a fixator 120 connected with the sealing disk 110. The fixator 120 includes a tubular component, and several supporting rods one end of which is connected with one end of the tubular component and the other end of which are diverging outwards in an umbrella-shape. The sealing disk 110 and the fixator 120 may be directly connected with each other or may be connected by a connecting component. The sealing disk 110 seals the opening of the left atrial appendage 200 at the entrance of the left atrial appendage 200, and the fixator 120 is fixed on the inner wall of the cavity of the left atrial appendage 200, so that the left atrial appendage occluder 100 is fixed on the left atrial appendage 200.

Figure 1:
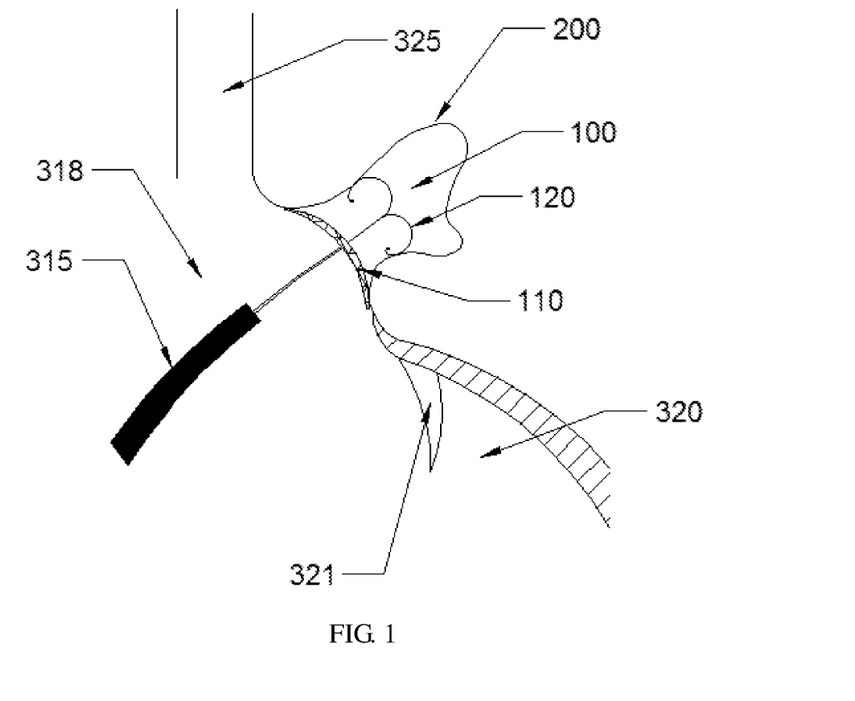
FIG. 1 is a schematic diagram of an image using the positive side of the proximal end of a medical device as a perspective view.

Before the surgery in this method for implanting the interventional medical device in the embodiment to implant the left atrial appendage occluder 100 in the vicinity of the opening of the left atrial appendage 200 of a human or animal body (hereinafter collectively referred to as "recipient"), the recipient should undergo detailed clinical examinations including assessment of clinical symptoms of atrial fibrillation, other cardiovascular diseases and new functional assessments (e.g. NYHA classification, i.e. classification of heart failure), cerebral apoplexy, and risk stratification of bleeding as well as the relevant laboratory tests in terms of routine blood, liver and kidney function, coagulation function, and the like.

In addition, TEE examination is also required before the surgery. The TEE examination includes: 1) confirming whether there is a thrombus in the left atrial appendage 200 and the left atrium; 2) measuring the size of the opening of the left atrial appendage 200 and the depth of the cavity of the left atrial appendage 200, so as to use the measurement result as a reference value for selecting a suitable model of medical device; and 3) assessing the shape of the left atrial appendage 200. When necessary, CT (Computed Tomography) or MRI (Magnetic Resonance Imaging) examinations are also needed to clarify the anatomical structure so as to further assist in determining whether the percutaneous left atrial appendage occlusion is suitable. It should be noted that, in this embodiment, different models of medical devices have different sizes. Generally, the corresponding models are selected according to the inner diameter of the cavity and the diameter of the opening of the left atrial appendage 200.

In another embodiment, the use of TEE may be avoided for preoperative examination. For example, methods such as TTE (Transthoracic Echocardiography) and bolus injection of contrast medium under fluoroscopy may be applied instead of TEE for examination. And after the surgery TTE or bolus injection of contrast medium can also be applied to replace the existing post-surgery steps which require the use of TEE, so as to avoid using TEE in the whole surgery. The operation involved in adopting TTE instead of TEE is a technique generally known to those technical personnel in this field and will not be described herein.

In the case of implantation in the human body as an example, during the course of surgery (abbreviated as in surgery), general anesthesia or local anesthesia may be selected for the patient, and local anesthesia may be preferred, depending on circumstances. It can be understood that non-anesthetic surgery may also be applied under some unfavorable conditions, if appropriate. Performing a femoral vein puncture on the patient after a local anesthesia to deliver the distal end of the puncture needle 316 into the right atrium 313 via the inferior vena cava 312. Preferably, delivering the sheath 315 into the superior vena cava 329 via the inferior vena cava 312 and through the right atrium 313 may be performed, and then the puncture needle 316 may be delivered via the sheath 315, whose position is determined by the visible marking points of sheath 315 under fluoroscopy, not exceeding the distal end of the sheath 315. Next, the step of locating the puncture site of the atrial septum 330 under X-ray fluoroscopy in the first perspective angle and the second perspective angle to use the puncture needle 316 to perform a puncture of the atrial septum 330 through the puncture site can be performed; and then the step of delivering the medical device to the left atrial appendage or left atrium for release under X-ray fluoroscopy in the first perspective angle can take place.

The position of the puncture site of the atrial septum 330 can be viewed through two special angles, which are the first perspective angle and the second perspective angle. Preferably, the first perspective angle is 30±5° to the right anterior oblique and the second perspective is left anterior oblique 45±5°. Compared with other perspective angles, these two perspective angles are favorable to locate a proper puncture site accurately and quickly.

During the puncture of atrial septum 330, generally, a position where fossa ovalis 314 can be avoided and the atrial septum 330 has a thick wall and the opening of left atrial appendage 200 can be reached after puncture is selected as a preferable puncture site. Specifically, locating the puncture site of the atrial septum 330 under X-ray fluoroscopy in the first perspective angle and the second perspective angle and using the puncture needle 316 to perform puncture of the atrial septum 330 through the puncture site include the following steps:

a.) Performing X-ray fluoroscopy in the angle of 45±5° to the left anterior oblique, and initially positioning the distal end of the puncture needle 316 to the position of the fossa ovalis 314. Specifically, after the puncture needle 316 is delivered to the sheath 315 at a position not exceeding its distal end, simultaneously withdrawing the sheath 315 and the puncture needle 316 so that they can synchronously slide along the atrial septum 330 toward the ventricle 311. When the jumping of the puncture needle 316 is observed from the image (which can also be sensed by the operator by contacting the part of the sheath 315 outside the human body), the head of the sheath 315 reaches the position of the fossa ovalis 314. In this case, referring to FIG. 2, when X-ray fluoroscopy is performed in the angle of 45±5° to left anterior oblique, the ascending aorta 310, the left atrial appendage 200, the ventricle 311, the inferior vena cava 312, the right atrium 313, the fossa ovalis 314, and the sheath 315, the pigtail catheter 317, the left atrium 318, and the superior vena cava 329 are all displayed on the image. At a perspective angle of 45±5° to left anterior oblique, the operator can clearly observe the contour of the atrial septum 330 from the perspective image.

Figure 2:
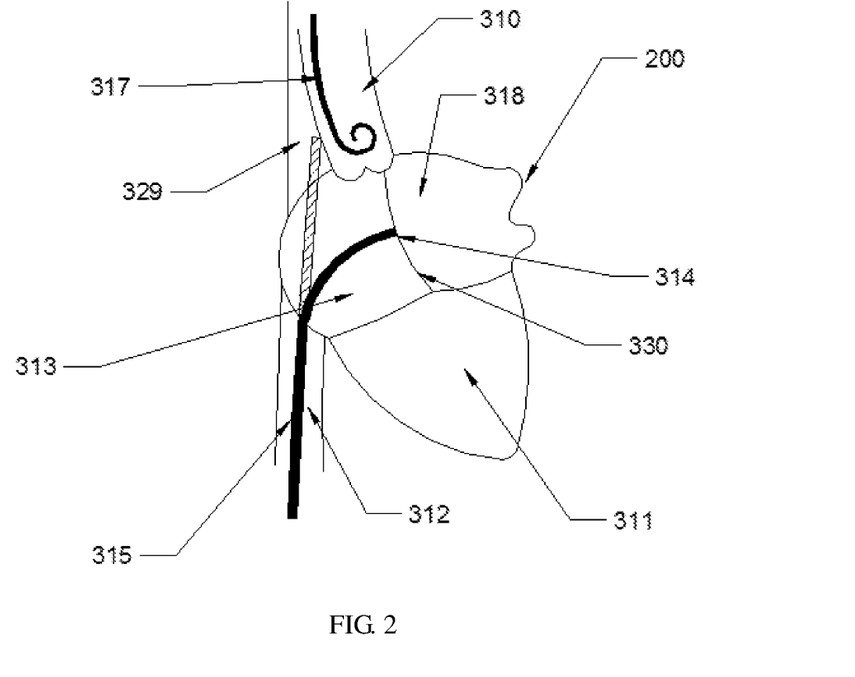
FIG. 2 is a schematic diagram of a heart structure image observed in a perspective view with an angle of 45° to the left anterior oblique.

Placing the pigtail catheter 317 in the ascending aorta 310. Since the pigtail catheter 317 is visible under fluoroscopy, it can be used to mark the position of the ascending aorta 310 so as to know the heart structure. It should be noted that placing the pigtail catheter 317 in the ascending aorta 310 contributes to the observation during the surgery. However, skipping the placement will not affect the result of the implanting surgery of the interventional medical device according to the method in the embodiment. In another embodiment, the pigtail catheter 317 is not placed in the ascending aorta 310.

Figure 3:
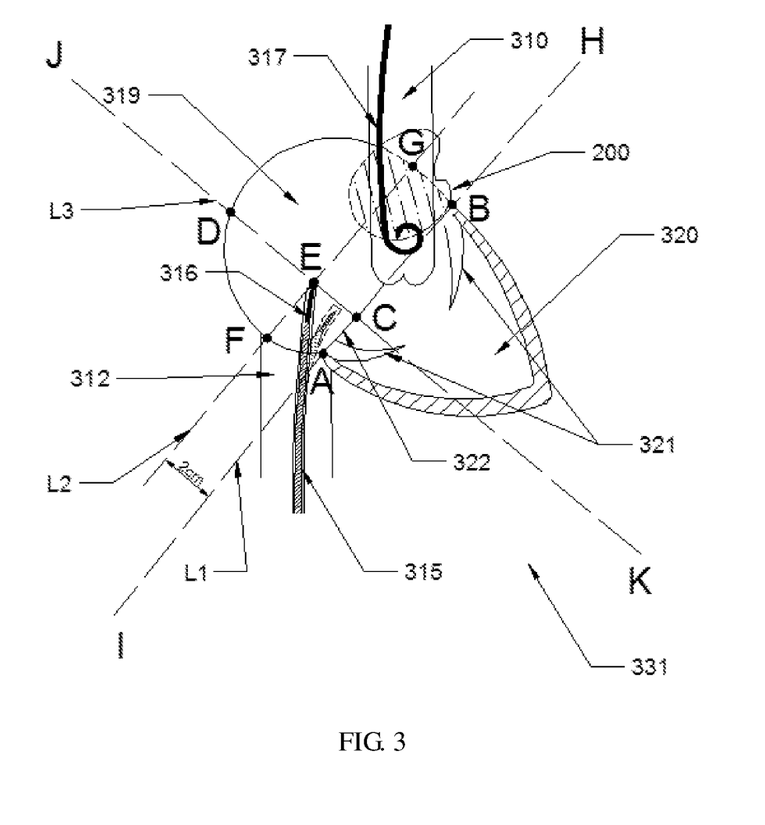
FIG. 3 is a schematic diagram of a heart structure image observed in a perspective view with an angle of 30° to the right anterior oblique.

In the present embodiment, an advantage of step a) is that the puncture needle 316 is initially positioned at fossa ovalis 314 so that the puncture site can be positioned accurately and quickly subsequently. It can be understood that in another embodiment, on the basis of sufficient perspective imaging measurement data, heart anatomy and other knowledge reserves, and actual surgical operation experience, step a) can be omitted. In this case, the puncture site can be just positioned by the X-ray fluoroscopy in a first perspective angle.

b.) The X-ray fluoroscopy is performed in an angle of 30±5° to the right anterior oblique and suitable reference objects are determined according to a visually-viewing heart part under X-rays so that the puncture site is determined in combination with an anatomical structure of the heart.

Please refer to FIG. 2 and FIG. 3. FIG. 3 is a structure diagram of the heart 331 observed from the image under X-ray fluoroscopy in an angle of 30±5° to the right anterior oblique. The image covers the ascending aorta 310, the atrium 319 observed from an angle of overlapping the left atrium 318 with the right atrium 313, the left atrial appendage 200, the left ventricle 320, the bicuspid valve 321, the atrioventricular sulcus 322, the inferior vena cava 312, the sheath 315, the pigtail catheter 317, and the heart 331. In addition, for the convenience of the following description, several auxiliary lines are drawn in FIG. 3, which are L1, the extended line of the atrioventricular sulcus 322; L2, the auxiliary line used to locate the puncture site; and L3, the auxiliary line perpendicular to the atrioventricular sulcus 322 from ⅓ of the length from the rear of the atrial septum 330. In FIG. 3, the shadow near the left atrial appendage 200 is the part of the left atrial appendage 200 shaded by the left atrium 318, the right atrium 313, and the ascending aorta 310; from the perspective image, the vertical distance between L1 and L2 is from the cross point of L1 and L3 and to the point located at ⅓ of the line segment extending along L3 toward the upper of the atrium from the cross point of L1 and L3 to the cross point of the line segment and the edge of atrium, i.e. the distance between the positions corresponding to these two auxiliary lines in the body of the patient is approximately 2 cm. At this time, the left atrium 318 overlaps the right atrium 313, so that the position of the atrioventricular sulcus 322 and part of left atrial appendage 200 that is above the atrioventricular sulcus 322 shown in the image can be observed.

The determination of the location of the puncture site includes: drawing back sheathing 315 and puncture needle 316 synchronously, and adjusting them to the designated puncture site, which is determined by the first cross point formed by the first segment and the third segment that is parallel with the second segment, and where the second segment is determined by the two endpoints formed by the cross of the straight line atrioventricular sulcus 322 is on with the heart's 331 boundary; the first segment is perpendicular to the second segment and their second cross point is ⅓ of the length of the second segment and close to the rear of the heart, and this second cross point is one of the endpoint of the first segment, the other endpoint of which is on the upper boundary of the atrium; and the distance from the first cross point to the second cross point is ⅓ of the length of the first segment.

Referring again to FIG. 3, the atrioventricular sulcus 322 can be viewed as a straight line under the current X-ray fluoroscopy (since the deviation is negligible and can therefore be regarded as a straight line), and this straight line the atrioventricular sulcus 322 is on forms two cross points with the boundary of the heart 331, point A (near the rear of the heart 331, i.e., direction I) and point B (near the front of the heart 331, i.e., direction H), and segment AB is the second segment AB, and at ⅓ of the length from point A on segment AB, point C, also the second cross point can be determined, and point C is at a place on the second segment AB where it's at ⅓ of the length from the rear direction I of the heart 331; point C is one endpoint of the first segment CD, which is perpendicular to the second segment AB, and the other end point, point D of the first segment CD is the cross point formed by the first segment CD and the upper boundary of the heart 331 (i.e., direction J), and segment CD is the first segment CD; at a place on segment CD where it's ⅓ of the length from the lower part of the heart 331 (i.e., direction K) point E can be determined, and point E is the first cross point, and the length of segment CE is ⅓ of segment CD, i.e., the distance from the first cross point, point E to the second cross point, point C (the length of segment CE) is ⅓ of the length of the first segment CD; the third segment FG passes point E and is parallel with segment AB, and the two cross points of the third segment FG with the boundary of the heart 331 are point F (near the rear of the heart 331) and point G (near the front of the heart 331). In FIG. 3, the first segment CD is on auxiliary line L3, the second line segment AB on auxiliary line L1, and the third segment FG on auxiliary line L2, and the auxiliary line L3 is at approximately ⅓ behind the atrial septum 330, and the auxiliary line L2 is approximately 2±0.5 cm above the atrioventricular sulcus 322. Thus, it can be estimated that the puncture site is at a place on the auxiliary line L3 where it is approximately at a position of ⅓ from the rear of the atrial septum 330, and where it is approximately at a position of ⅓ from the atrioventricular sulcus 322 on the section from atrioventricular sulcus 322 to the atrium 319 on the same auxiliary line. In addition, the position of the puncture site can be confirmed or finely adjusted by referencing to the location where the sheath 315 enters the right atrium 313 via the inferior vena cava 312 and the location of the center of the left atrial appendage 200's opening on the image as estimated based on atrioventricular sulcus 322, using the theory that two points forms a line.

Figure 4:
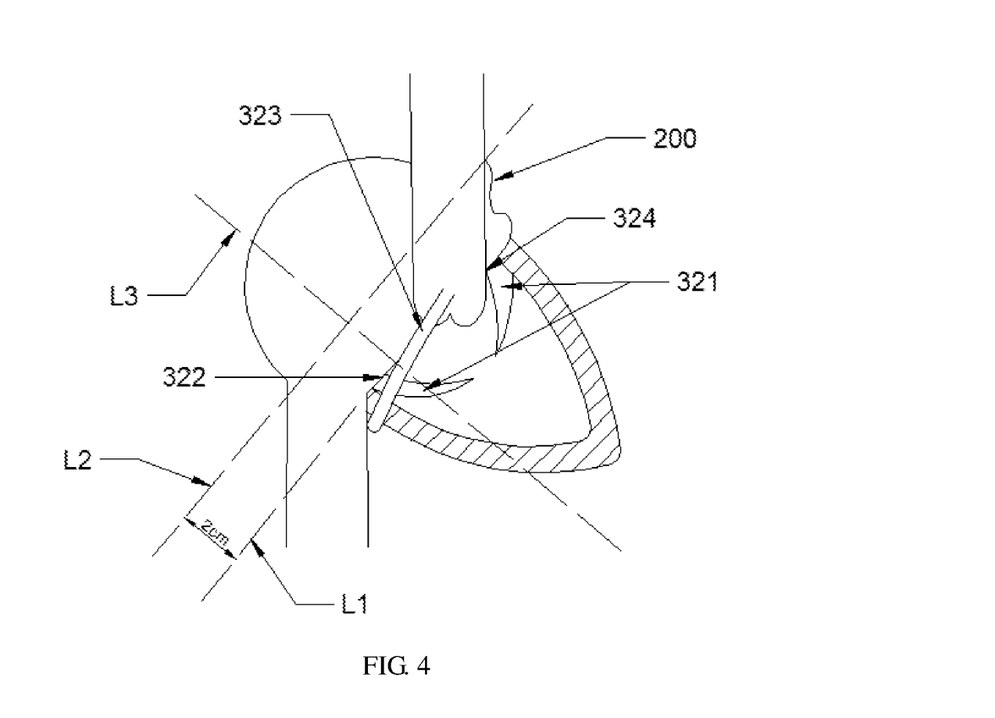
FIG. 4 is a schematic diagram of an image in which the available reference objects are observed and selected using a perspective view with an angle of 30° to the right anterior oblique.

Please refer to FIG. 4, which is a schematic perspective view of the right anterior oblique 30±5° position. From the schematic view, it can be seen that the position of atrioventricular sulcus 322 can be determined using just as a reference object without other tools. Moreover, the position of the atrioventricular sulcus 322 can be further confirmed through the calcified right coronary artery trunk 323 and the calcified mitral ring 324. For the convenience of the following description, several auxiliary lines are drawn in FIG. 4, which are L1, the extended line of the atrioventricular sulcus 322; L2, the auxiliary line used to locate the puncture site; and L3, the auxiliary line perpendicular to the atrioventricular sulcus 322 from ⅓ of the length from the rear of the atrial septum 330. Since the atrioventricular sulcus 322 mainly consists of fat, the atrioventricular sulcus 322, under the X-ray fluoroscopy, is shown as a bright line and can be used as a reference subject for positioning the puncture site. The right coronary artery trunk 323 is distributed in the atrioventricular sulcus 322 and the coronary sulcus. Calcification of the right coronary artery trunk 323 can be observed under the fluoroscopic image, so by observing the calcified right coronary artery trunk 323, the trending of the coronary artery and the structure of the patient's heart 331 can be determined. Since the opening of the left atrial appendage 200 is located above the bicuspid valve 321 in most cases, observation of the calcified mitral ring 324 through X-ray fluoroscopy, and determination of the location of calcified mitral ring 324 can be helpful to determine the position of the atrioventricular sulcus 322 or the opening of the left atrial appendage 200.

c.) Moving the distal end of the puncture needle 316 from the fossa ovalis 314 to the puncture site and adjusting it to be perpendicular to the direction of the atrial septum 330 for puncture. And at this moment, the distal end of the puncture needle 316 substantially corresponds to the center of the opening of the left atrial appendage 200. During the puncturing process, when it feels that the puncture needle 316 is falling into a void, it means that the puncture is successful and can be confirmed by injecting contrast medium. Before the puncture site is located and the atrial septum 330 puncture is performed, measurement data such as the structural features of the patient's left atrium 318 and right atrium 313 can be acquired by delayed imaging. For example, when the data of the patient's left atrial appendage 200 acquired before surgery is insufficient, or the relevant data needs to be supplemented during the surgery, a contrast medium may be injected in the right atrium 313 or in the mouth of the pulmonary artery and wait for 5-10 seconds until the contrast medium flows into the left atrium 318 via the pulmonary arteriovenous, and then imaging data on the left atrium 318 and the right atrium 313 can be observed clearly under the X-ray.

Before performing the puncture, the distal end of the puncture needle 316 can be adjusted to a position perpendicular to the atrial septum 330, and then puncture the atrial septum 330. By doing so, the distal end of the puncture needle 316 can be directed to the opening of the left atrial appendage 200, which will later facilitate to transport the left atrial appendage occluder 100_inside the left atrial appendage 200 for release. In another embodiment, prior to the puncture, the approximate position of the left atrial appendage 200 can be determined through references such as the atrioventricular sulcus 322 by observing the intraocular fluoroscopic image during the surgery, so as to adjust the direction of the puncture needle 316 to the opening of the left atrial appendage 200, and then puncture at the puncture site selected, ensuring the sheath 315 can still face the opening of the left atrial appendage 200 after it passes by this puncture site.

In the traditional left atrial appendage occlusion, the operator first positions the ideal positioning point based on a theoretically ideal positioning point located at a rear and lower place of the atrial septum 330, and then positions this ideal positioning point relying on TEE. However, since the structure of the left atrial appendage 200 varies significantly, the position of the opening of the left atrial appendage 200 is very likely to vary. Therefore, the theoretically ideal puncture site may not be applicable to most patients, and there are cases where the device cannot be placed. In the present embodiment, the puncture direction of the puncture needle 316 is first adjusted to be aligned with the position of the opening of the left atrial appendage 200, and then the puncture is performed according to a suitable puncture point obtained by positioning, and after the puncture is performed, the sheath 315 that contains the puncture needle 316 can still properly face to the opening of the left atrial appendage 200, ensuring quick and accurate placement of the medical device.

Figure 5:
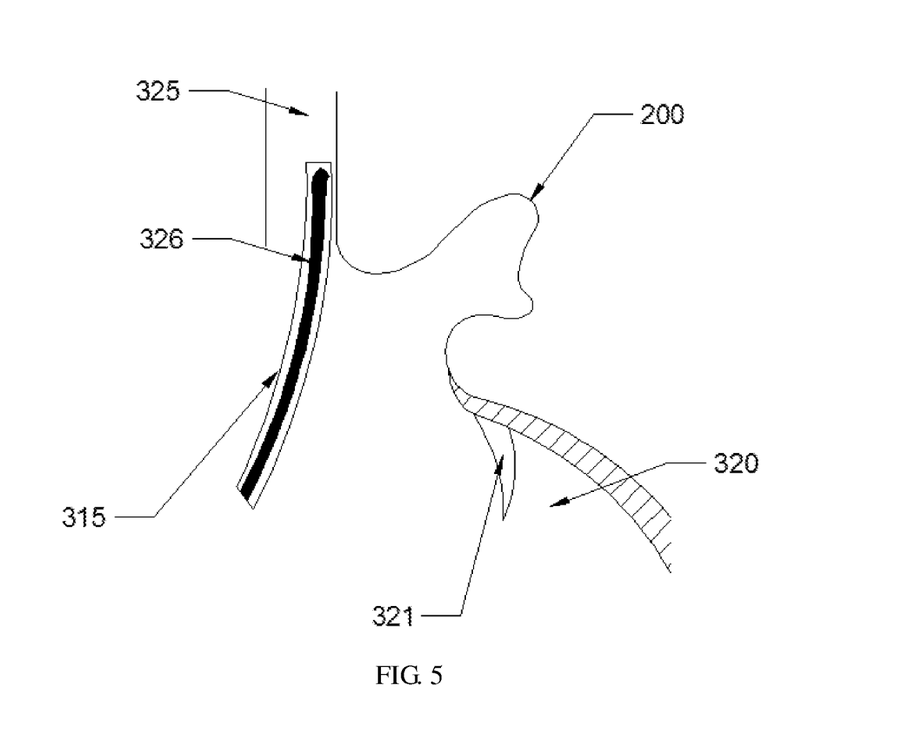
FIG. 5 is a schematic diagram of another image of the heart structure observed in a perspective view with an angle of 30° to the right anterior oblique.
Figure 6:
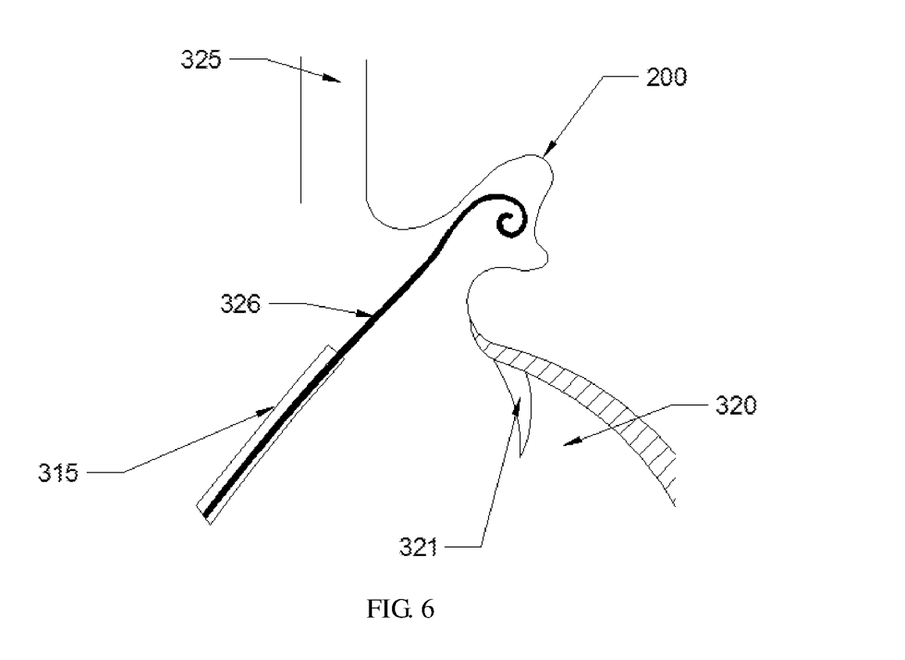
FIG. 6 is a schematic diagram of another image of the heart structure observed in a perspective view with an angle of 30° to the right anterior oblique.

After puncturing the atrial septum 330, the sheath 315 can be transported to the left upper pulmonary vein 325, and there withdraw the puncture needle 316 from the sheath 315, and then put the pigtail contrast catheter 326, via the sheath 315, into the left upper pulmonary vein 325, please refer to FIG. 5. Next, synchronously withdraw the sheath 315 and the pigtail contrast catheter 326 to transport them to the left atrial appendage 200 for imaging; select the proper size of left atrial appendage occluder 100 based on the structural features of the patient's left atrial appendage 200 observed through the image and the size of the opening and the depth of the cavity of the left atrial appendage 200 measured before or re-measured during the surgery, and then prepare the implant, i.e., prepare the left atrial appendage occluder 100 in accordance with the specifications for the interventional devices. First, push out the pigtail contrast catheter 326 from inside the sheath 315 and place it inside the left atrial appendage 200, and then transport along the pigtail contrast catheter 326 the distal end of the sheath 315 to the inside of the left atrial appendage 200. Please refer to FIG. 6. After the sheath 315 is in place, withdraw the pigtail contrast catheter 326, and put the left atrial appendage occluder 100 in, during which process, the left atrial appendage implant 100 is contained inside the outer sheath and both are transported to the left atrial appendage 200 via the sheath 315. Next, select a place near the opening of the left atrial appendage 200 to place the left atrial appendage occluder 100.

Figure 7:
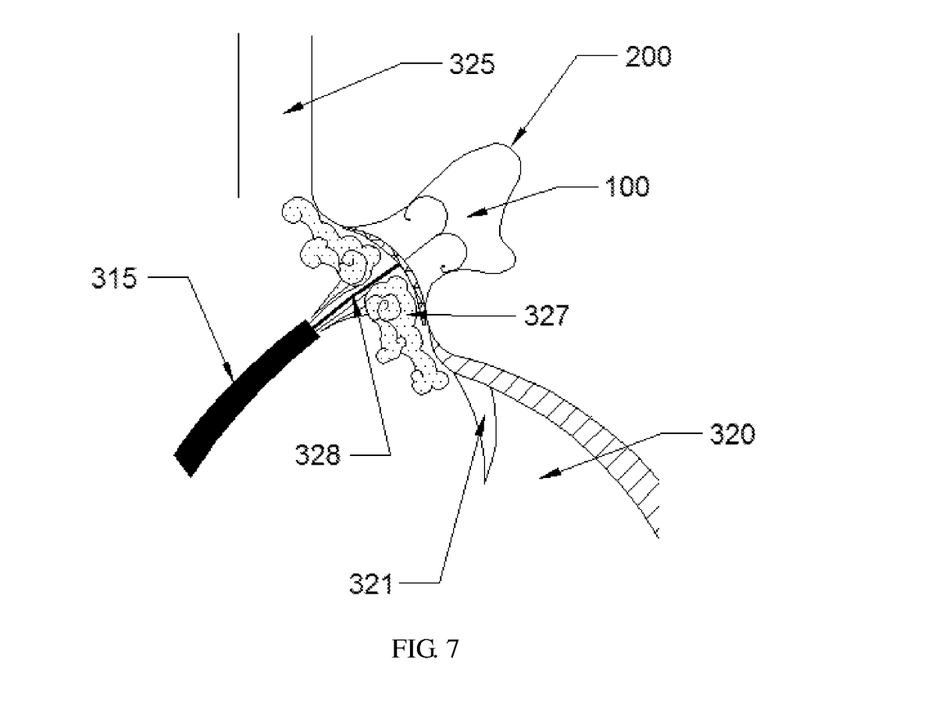
FIG. 7 is a schematic diagram of an image assisting in determining the sealing and the interference of the device after the bolus injection of the contrast medium.

Please refer to FIG. 1 again, which shows the perspective image of the positive side of the proximal end of left atrial appendage occluder 100. From the image, it can be seen that the contents include the left upper pulmonary vein 325, the left atrial appendage 200, the left atrial appendage occluder 100, the bicuspid valve 321, the sheath 315, the left ventricle 320, and the left atrium 318. FIG. 7 is a schematic diagram for judging the hermeticity of and interference to the left atrial appendage occluder 100 after injection of a contrast medium. The contents displayed include the contrast medium 327, the left upper pulmonary vein 325, the left atrial appendage 200, the left atrial appendage occluder 100, the left ventricle 320, the bicuspid valve 321 and the sheath 315.

The left atrial appendage occluder 100 has its proximal end connected to the distal end of the transport rod 328 during the implantation. Please refer to FIG. 7 again, when assessing the effect of the implantation of the left atrial appendage occluder 100, the hermeticity of the medical device can be examined, before the release of the left atrial appendage occluder 100 from the transport rod 328 (e.g., a transport wirerope) by injecting contrast medium 327 from at least two different angles. When the viewing angle is adjusted to the positive side of the proximal end of the medical device, sealing problems at any point near the proximal end of the medical device can be observed, eliminating the need to change the angle for inspection. Preferably, a contrast medium 327 is injected from two observation angles having a 90° difference to assess the hermeticity of the medical device. Since the positive side of the medical device is selected for observation, if there is a residual flow, the contrast medium 327 can be observed on the image to flow into the left atrial appendage 200 via the left atrial appendage occluder 100. Generally, the residual blood flow is acceptable when it is less than 5 mm, and thereby the hermeticity of the medical device can be assessed.

When the contrast medium 327 is injected, the positional relationship between the edge of the medical device and the mouth of the left upper pulmonary vein 325 and the bicuspid valve 321 can also be observed, and thereby whether or not the interface to the device occurs can be assessed. In addition, the stability of the left atrial appendage occluder 100 after its implantation can also be assessed by a pull test, and based on the actual condition, the device can be adjusted and then released.

After confirming that the effect of the implantation of the left atrial appendage occluder 100 is good, remove all the auxiliary devices, such as the sheath 315 and the transport rod 328, except the left atrial appendage occluder 100, after the left atrial appendage occluder 100 is disconnected from the transport rod 328, and then the surgery process ends.

In the implanting method in the present embodiment, after puncturing the femoral vein, an interventional medical device can accurately locate the puncture site only through X-ray fluoroscopy under two different perspective angles, completely replacing the conventional left atrial appendage occlusion that is required to use TEE to locate the puncture site for atrial septum 330. In addition, during the surgery, the recipients do not need to receive general anesthesia but only local anesthesia. It requires no cooperation from anesthesiologists, reducing the waste of manpower, simplifying the surgical procedure, and reducing the inconvenience of cooperation between the various departments, and the recipients are conscious so that the status of the recipients can be observed and learned any time. If an accident occurs, it can be detected immediately, reducing the suffering of the recipients and improving the safety of the surgery.

On the other hand, the existing surgical method for the left atrial appendage occlusion is considered to be one of the most complicated interventions, which requires the physician and the entire surgical team to be well-trained; as a result, the left atrial appendage occlusion can only be performed at hospitals with certain conditions available. Due to the complication of the operation, the time (approximately 60 minutes) of the surgery, and demanding requirements for the surgical environment, the traditional occlusion can only be performed under certain conditions and cannot be widely used. The implantation method in the present embodiment does not require the use of TEE nor general anesthesia during the surgery, thereby reducing unnecessary operations and reducing the difficulty of surgery. The surgery can be performed on the patients in their conscious state, increasing the safety of the surgery, making the operation less complicated, and reducing the time needed for the surgery (from the clinical outcomes, the surgery can be completed within 30 minutes), and it is also less demanding for operating room equipments, therefore, it can be widely used.

The technical features of the above-described embodiments can be combined arbitrarily. To make the description succinct, all the possible combinations of the technical features in the above embodiments are not described. However, all combinations shall be considered as described in the Specification as long as no contradiction exists in the combination of these technical features.

The embodiments described above are merely illustrative of several embodiments of the disclosure. The description is more specific and detailed, but the embodiments shall not be construed as the limitation of the scope of the disclosure as claimed. It shall be noted that several variants and improvements can be made without departing from concept of the disclosure for ordinary persons skilled in the art, which are within the scope of protection of the disclosure. Accordingly, the scope of protection of the disclosure shall be subject to the claims set forth.

What is claimed:

1. A method for implanting an interventional medical device, comprising: delivering a distal end of a puncture needle into a right atrium via an inferior vena cava; locating a puncture site on an atrial septum under X-ray fluoroscopy in a first perspective angle and a second perspective angle, and puncturing the atrial septum by the puncture needle through the puncture site;
   delivering the medical device to a left atrial appendage or a left atrium for release under X-ray fluoroscopy in the first perspective angle; wherein the second perspective angle is 45±5° to a left anterior oblique so that the puncture needle is initially positioned at a fossa ovalis, and the first perspective angle is 30±5° to a right anterior oblique so that a position of the atrioventricular sulcus is determined using just as a reference object without other tools, so that the puncture site is positioned subsequently with the first and second perspective angles.

2. The method for implanting an interventional medical device of claim 1, further comprising, before the step of delivering the distal end of the puncture needle into the right atrium via the inferior vena cava, puncturing a femoral vein after local anaesthesia is administered to a recipient.

3. The method for implanting an interventional medical device of claim 2, wherein before the step of puncturing the femoral vein after local anaesthesia is administered to the recipient, performing preoperative examinations on the recipient to obtain required measurement data.

4. The method for implanting an interventional medical device of claim 3, wherein the required measurement data comprises at least the size of the left atrial appendage's opening and the depth of the left atrial appendage's cavity.

5. The method for implanting an interventional medical device of claim 3, wherein the preoperative examination comprises one of the followings: a TEE examination, a TTE examination, and an examination using bolus injection contrast medium.

6. The method for implanting an interventional medical device of claim 1, wherein the step of locating the puncture site on atrial septum under X-ray fluoroscopy in a first perspective angle and a second perspective angle, and puncturing the atrial septum by the puncture needle through the puncture site comprises:
   performing X-ray fluoroscopy in the second perspective angle, and initially positioning the distal end of the puncture needle to a position of a fossa ovalis;
   performing X-ray fluoroscopy in the first perspective angle, viewing the atrioventricular sulcus as a reference object under X-rays, and determining a puncture site in combination with the reference object and an anatomical structure of the heart;
   moving the distal end of the puncture needle from the fossa ovalis to the puncture site, adjusting it to be perpendicular to the atrial septum, and puncturing the atrial septum.

7. The method of implanting an interventional medical device of claim 6, wherein the position of the puncture site is determined by a first cross point formed by a first segment and a third segment that is parallel with a second segment, and wherein the second segment is determined by two endpoints formed by a cross of a straight line atrioventricular sulcus is on with a heart boundary; the first segment is perpendicular to the second segment and their second cross point is at ⅓ of a length of the second segment and proximate to a rear of the heart, and the second cross point is one of the endpoint of the first segment, the other endpoint of which is on an upper boundary of the atrium; and a distance from the first cross point to the second cross point is ⅓ of the length of the first segment.

8. The method for implanting an interventional medical device according of claim 6, wherein the puncture needle is contained in a sheath, and the step of delivering the medical device to the left atrial appendage or the left atrium for release under X-ray fluoroscopy in the first perspective angle comprises:
   moving a sheath to a left upper pulmonary vein; withdrawing the puncture needle from the sheath in the left upper pulmonary vein; after performing the radiography in the left atrial appendage or the left atrium, delivering the distal end of the sheath into the left atrial appendage or the left atrium; delivering the medical device via the sheath and releasing the medical device near the left atrial appendage or the left atrium.

9. The method for implanting an interventional medical device of claim 1, wherein the interventional medical device is a left atrial appendage occluder.

10. The method for implanting an interventional medical device of claim 1, wherein the medical device is connected with a transport rod during an implantation process, and the implanting method further comprises:

after releasing the medical device and before disconnecting it with the transport rod, injecting a contrast medium from at least two different viewing angles to assess the hermeticity of the medical device.

11. The method of implanting an interventional medical device of claim 10, wherein a positive side position of the proximal end of the medical device is selected for observation, and the contrast medium is injected with two observation angles in 90 degrees difference to assess the hermeticity of the medical device.

12. The method for implanting an interventional medical device of claim 1, wherein the medical device is connected with a transport rod during an implantation process, and the implanting method comprises:

after releasing the medical device and before disconnecting it with the transport rod, injecting a contrast medium and at the same time observing a positional relationship between an edge of the medical device and a left upper pulmonary vein ostium and a bicuspid valve to determine whether interference by the device occurs.

13. The method for implanting an interventional medical device of claim 1, further comprising, before the step of locating the puncture site on atrial septum under X-ray fluoroscopy in a first perspective angle and a second perspective angle, and puncturing the atrial septum by the puncture needle through the puncture site, performing a bolus injection of contrast medium into the right atrium or pulmonary artery, and observing structure of the left atrium for 5-10 seconds after the bolus injection to obtain desired measurement data.

\* \* \* \* \*